US00PP23928P2

(12) United States Plant Patent
Dümmen

(10) Patent No.: US PP23,928 P2
(45) Date of Patent: Sep. 24, 2013

(54) ***PETUNIA* PLANT NAMED 'DUESWEBLASAT'**

(50) Latin Name: *Petunia×hybrida*
Varietal Denomination: Duesweblasat

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 76 days.

(21) Appl. No.: 13/374,102

(22) Filed: Dec. 9, 2011

(51) Int. Cl.
*A01H 5/00* (2006.01)

(52) U.S. Cl.
USPC ..... Plt./356.1

(58) Field of Classification Search
USPC ..... Plt./356.1
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'Duesweblasat', characterized by its semi-upright and mounding plant habit; freely branching habit; early and freely flowering habit; large black-colored flowers; and good garden performance.

1 Drawing Sheet

Botanical designation: *Petunia×hybrida*.
Cultivar denomination: 'DUESWEBLASAT'.

BACKGROUND OF THE INVENTION

The present invention relates to a new and distinct cultivar of *Petunia* plant, botanically known as *Petunia×hybrida* and hereinafter referred to by the name 'Duesweblasat'.

The new *Petunia* plant is a product of a planned breeding program conducted by the Inventor in Rheinberg, Germany. The objective of the breeding program is to create new compact *Petunia* plants with numerous unique and attractive flowers.

The new *Petunia* plant originated from a cross-pollination made by the Inventor in January, 2010 in Rheinberg, Germany of a proprietary selection of *Petunia×hybrida* identified as code number T04-0067-7, not patented, as the female, or seed, parent with a proprietary selection of *Petunia×hybrida* identified as code number F-02-2205, not patented, as the male, or pollen, parent. The new *Petunia* plant was discovered and selected by the Inventor as a single flowering plant within the progeny of the stated cross-pollination in a controlled greenhouse environment in Rheinberg, Germany in May, 2011.

Asexual reproduction of the new *Petunia* plant by terminal cuttings in a controlled greenhouse environment in Rheinberg, Germany since June, 2011 has shown that the unique features of this new *Petunia* plant are stable and reproduced true to type in successive generations.

SUMMARY OF THE INVENTION

Plants of the new *Petunia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Duesweblasat'. These characteristics in combination distinguish 'Duesweblasat' as a new and distinct *Petunia* plant:

1. Semi-upright and mounding plant habit.
2. Freely branching habit.
3. Early and freely flowering habit.
4. Large black-colored flowers.
5. Good garden performance.

Plants of the new *Petunia* can be compared to plants of the female parent selection. Plants of the new *Petunia* differ primarily from plants of the female parent selection in the following characteristics:

1. Plants of the new *Petunia* are not as compact as plants of the female parent selection.
2. Plants of the new *Petunia* have larger flowers than plants of the female parent selection.
3. Flowers of plants of the new *Petunia* are darker in color than flowers of plants of the female parent selection.

Plants of the new *Petunia* can be compared to plants of the male parent selection. Plants of the new *Petunia* differ primarily from plants of the male parent selection in the following characteristics:

1. Plants of the new *Petunia* are more compact than plants of the male parent selection.
2. Plants of the new *Petunia* have smaller and more rounded flowers than plants of the male parent selection.

Plants of the new *Petunia* can be compared to plants of the *Petunia×hybrida* 'Balpevac', U.S. Plant Pat. No. 22,666. In side-by-side comparisons conducted in Rheinberg, Germany, plants of the new *Petunia* differed primarily from plants of 'Balpevac' in the following characteristics:

1. Plants of the new *Petunia* were more compact than plants of 'Balpevac'.
2. Plants of the new *Petunia* had smaller leaves than plants of 'Balpevac'.
3. Plants of the new *Petunia* had smaller and more rounded flowers than plants of 'Balpevac'.

BRIEF DESCRIPTION OF THE PHOTOGRAPH

The accompanying colored photograph illustrates the overall appearance of the new *Petunia* plant showing the colors as true as it is reasonably possible to obtain in colored reproductions of this type. Colors in the photograph may differ slightly from the color values cited in the detailed botanical description which accurately describe the colors of the new *Petunia* plant. The photograph comprises a side perspective view of a typical flowering plant of 'Duesweblasat' grown in a container.

DETAILED BOTANICAL DESCRIPTION

The aforementioned photograph and following observations, measurements and values describe plants grown in 12-cm containers during the summer in a glass-covered greenhouse in Rheinberg, Germany and under cultural practices typical of commercial potted *Petunia* production. During the production of the plants, day and night temperatures averaged 18° C. and light levels averaged 4,500 lux. Plants were pinched one time three weeks after planting and were 16 weeks old when the photograph and description were taken. In the following description, color references are made to The Royal Horticultural Society Colour Chart, 1995 Edition, except where general terms of ordinary dictionary significance are used.

Botanical classification: *Petunia×hybrida* 'Duesweblasat'.

Parentage:

*Female, or seed, parent*.—Proprietary selection of *Petunia×hybrida* identified as code number T04-0067-7, not patented.

*Male, or pollen, parent*.—Proprietary selection of *Petunia×hybrida* identified as code number F-02-2205, not patented.

Propagation:

*Type*.—By terminal cuttings.

*Time to initiate roots, summer*.—About five days at temperatures of about 20° C.

*Time to initiate roots, winter*.—About seven days at temperatures of about 20° C.

*Time to produce a rooted young plant, summer*.—About three weeks at temperatures of about 20° C.

*Time to produce a rooted young plant, winter*.—About four weeks at temperatures of about 20° C.

*Root description*.—Fine, fibrous; white in color.

*Rooting habit*.—Freely branching; dense.

Plant description:

*Plant and growth habit*.—Semi-upright and mounding plant habit; freely branching habit with about eight to ten lateral branches developing after pinching; moderately vigorous growth habit.

*Plant height*.—About 15 cm.

*Plant diameter*.—About 25.5 cm.

Lateral branch description:

*Length*.—About 16 cm.

*Diameter*.—About 4.5 mm.

*Internode length*.—About 2 cm.

*Strength*.—Moderately strong.

*Aspect*.—Initially upright to outwardly spreading.

*Texture*.—Pubescent.

*Color*.—Close to 144A to 144B.

Foliage description:

*Arrangement*.—Before flowering begins, leaves are alternate, simple; after flowering begins, leaves are opposite, simple.

*Length*.—About 3,7 cm.

*Width*.—About 1.7 cm.

*Shape*.—Spatulate.

*Apex*.—Obtuse.

*Base*.—Attenuate.

*Margin*.—Entire.

*Texture, upper and lower surfaces*.—Pubescent; leathery.

*Venation pattern*.—Pinnate; arcuate.

*Color*.—Developing and fully expanded leaves, upper surface: Close to 146A; venation, close to 146D. Developing and fully expanded leaves, lower surface: Close to 146B; venation, close to 146A.

*Petioles*.—Length: About 3 mm. Diameter: About 3 mm. Texture, upper and lower surfaces: Pubescent. Color, upper surface: Close to 146C. Color, lower surface: Close to 146D.

Flower description:

*Flower arrangement and habit*.—Single salverform flowers arising from leaf axils; freely flowering habit with usually about 25 to 30 open flowers and flower buds per plant; flowers face mostly upright to outwardly.

*Fragrance*.—None detected.

*Natural flowering season*.—Plants flower continuously during the spring and summer in Germany; early flowering habit, plants typically beginning flowering about nine weeks after planting.

*Flower longevity*.—Individual flowers last about five to seven days on the plant; flowers persistent.

*Flower diameter*.—About 6 cm.

*Flower length (height)*.—About 4.9 cm.

*Flower throat diameter*.—About 1.1 cm.

*Flower tube length*.—About 3 cm.

*Flower tube diameter*.—About 3 mm.

*Flower bud*.—Length: About 4.5 cm. Diameter: About 6 mm. Shape: Ovoid. Color: Close to 200A.

*Corolla*.—Arrangement: Five petals fused at the base and opening into a flared trumpet. Petal lobe length (from throat): About 3 cm. Petal lobe width: About 2.7 cm. Petal shape: Roughly spatulate. Petal apex: Rounded. Petal margin: Entire. Petal texture, upper and lower surfaces: Rippled, glabrous. Throat texture: Rippled, glabrous. Tube texture: Rippled, pubescent. Color: Petal lobe, when opening, upper and lower surfaces: Close to 200A. Petal lobe, fully opened, upper surface: Close to 202A; venation, close to 202A; color does not fade with development. Petal lobe, fully opened, lower surface: Close to 79A; venation, close to 79A. Flower throat: Close to 202A; venation, close to 202A. Flower tube: Close to 79A; venation, close to 79A.

*Calyx*.—Arrangement: Five sepals fused at the base forming a star-shaped calyx. Sepal length: About 1.6 cm. Sepal width: About 3.5 mm. Sepal shape: Oblong. Sepal apex: Rounded. Sepal margin: Entire. Sepal texture, upper and lower surfaces: Smooth. Color, immature and mature, upper surface: Close to 147A. Color, immature and mature, lower surface: Close to 146B.

*Peduncles*.—Length: About 3.5 cm. Diameter: About 2.9 mm. Strength: Moderately strong. Texture: Smooth. Color: Close to 144A.

*Reproductive organs*.—Stamens: Quantity: Five per flower. Filament length: About 1.25 cm. Filament color: Close to 72A. Anther shape: Ovate. Anther length: About 1 mm. Anther color: Close to 198B. Pollen amount: Abundant. Pollen color: Close to 202C. Pistils: Quantity: One per flower. Pistil length: About 2.4 cm. Style length: About 1.8 cm. Style color:

Close to 145A. Stigma shape: Rounded. Stigma color: Close to 144A. Ovary color: Close to 83B. Seeds and fruits: Seed and fruit development have not been observed on plants of the new *Petunia*.

Garden performance: Plants of the new *Petunia* have been observed to have good garden performance and tolerate wind, rain and temperatures ranging from about 5° C. to about 40° C.

Pathogen & pest resistance: Plants of the new *Petunia* have not been observed to be resistant to pathogens and pests common to *Petunia* plants.

It is claimed:

1. A new and distinct *Petunia* plant named 'Duesweblasat' as illustrated and described.

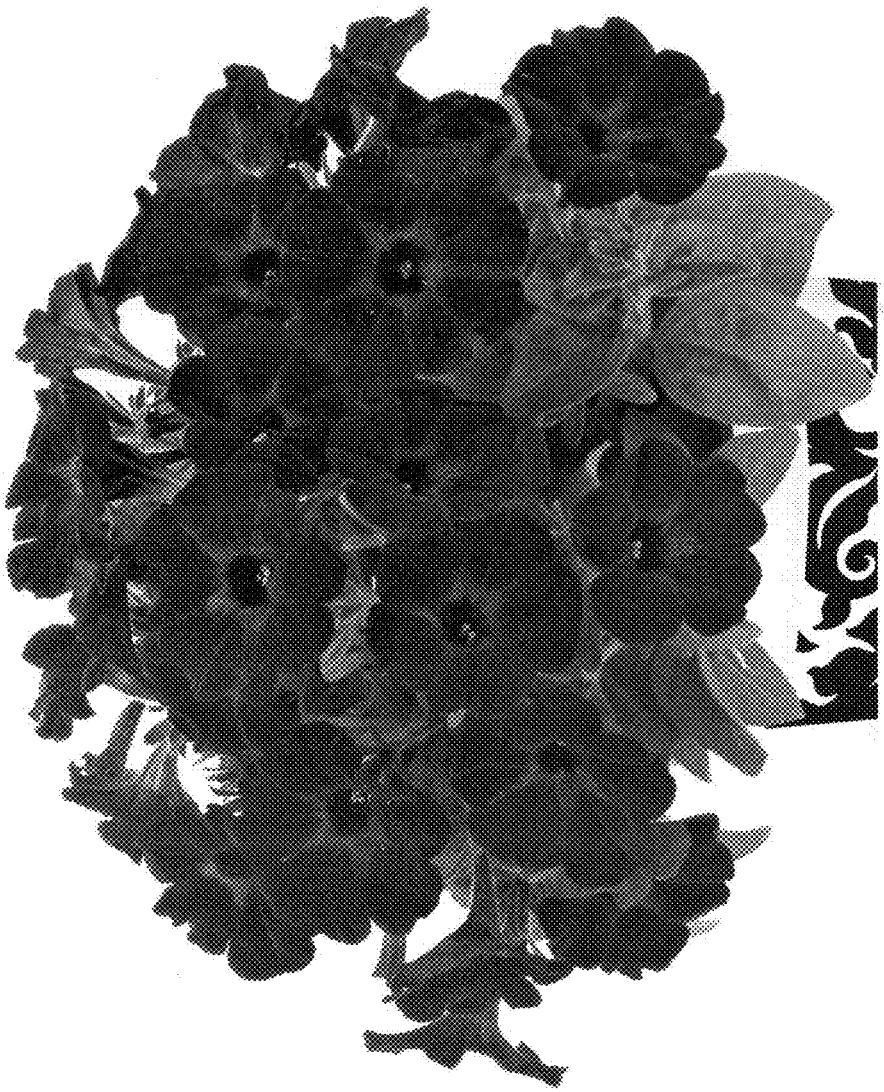

* * * * *